US00PP17203P3

(12) United States Plant Patent
Shibamichi

(10) Patent No.: US PP17,203 P3
(45) Date of Patent: Nov. 14, 2006

(54) **PLANT VARIETY OF *DAVIDIA INVOLUCRATA* NAMED 'PURPLELEAF'**

(50) Latin Name: *Davidia involucrata*
Varietal Denomination: Purpleleaf

(75) Inventor: Akira Shibamichi, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/984,267

(22) Filed: Nov. 8, 2004

(65) Prior Publication Data

US 2006/0101550 P1 May 11, 2006

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
*Assistant Examiner*—Annette H Para
(74) *Attorney, Agent, or Firm*—Christie, Parker & Hale, LLP

(57) ABSTRACT

A new plant variety of *Davidia involucrata* distinguished from its parents and all other varieties of *Davidia involucrata* of which I am aware by the dark burgundy colored foliage in spring through leaf abscission in fall.

1 Drawing Sheet

Figure 1:
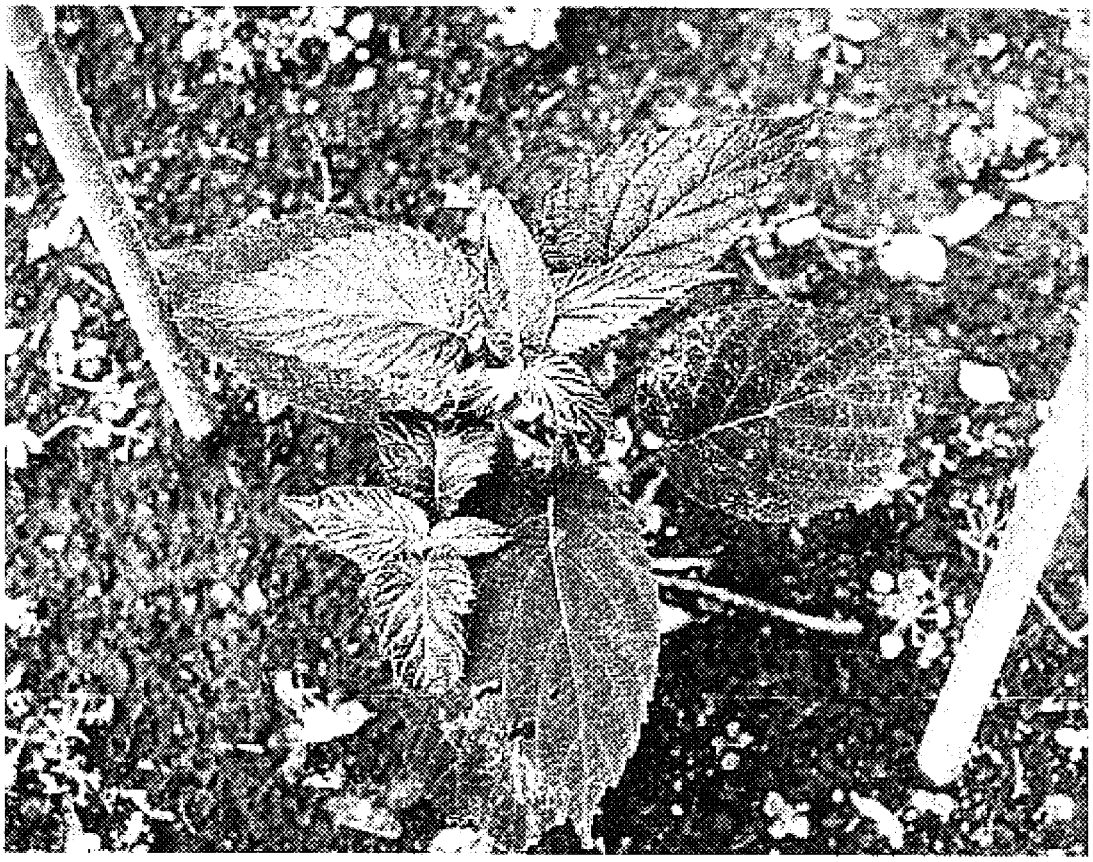

Botanical classification: *Davidia involucrata* (Baill.).
Varietal name: 'Purpleleaf'.

BACKGROUND OF THE INVENTION

The present invention relates to a new and distinct variety of *Davidia involucrata,* which was developed in a controlled breeding program in Kawaguchi City, Japan, by the originator Mr. Akira Shibamichi. The varietal denomination of the new variety is 'Purpleleaf'.

The genus *Davidia* is included in the family Davidiaceae, which comprises one genus and one species originating in Western China. *Davidia involucrata* is uncommon in its native habit of Western China. It generally has a habit of a 20 meter tall deciduous tree with a dominant central leader, branches thick, glabrous. Leaf color is green, depending on light intensity and cultural conditions. Leaves are generally broadly ovate, 8 to 24 cms long, cordate at base, dentate, glossy and glabrous above, densely gray tomentose beneath. Petioles are 4 to 5 cms long, red, flowers are about 2 cm wide, surrounded by 2 opposite, uneven sized, 8 to 16 cm long, pendulous, yellowish white involucral leaves. Plant blooms May to June on older, mature specimens often more than 20 years in age. Fruits are ellipsoid, about 2.5 cms long.

SUMMARY OF THE INVENTION

The new variety was discovered as an open pollinated seedling in a controlled planting of *Davidia involucrata.* The new variety differs from its parents in bearing dark burgundy colored foliage in spring and continuing through leaf abscission in fall. Asexual reproduction of the new variety in Kawaguchi City, Japan by grafting has confirmed that the distinctive characteristics of the new variety are stable and reproduced true to type in successive generations of asexual propagation.

COMPARISON WITH PARENTS

'Purpleleaf' is distinguished from its parents and all other varieties of *Davidia involucrata* of which I am aware, including the specific variety, *Davidia involucrata* var. *Vilmoriniana* (not patented) by the dark burgundy colored foliage in spring through leaf abscission in fall.

BRIEF DESCRIPTION OF ILLUSTRATIONS

The accompanying illustrations show a specimen of the new cultivar in a photo illustration as true to color as is reasonably possible to make in an illustration of this character.

FIG. 1 illustrates the distinctive foliage of the new variety.

DETAILED DESCRIPTION OF THE NEW VARIETY

'Purpleleaf' has not been observed under all possible environmental, cultural and light conditions. The following observations and descriptions are of plants grown in Kawaguchi City, Japan and Vacaville, Calif. In this description, color references are to The Royal Horticultural Society Colour Chart (2002) and terminology used in the color descriptions herein refers to plate numbers in this color chart. Phenotypic expression may vary with light intensity, cultural and environmental conditions.

Classification:
- *Botanical.*—*Davidia involucrata* (Baill.) 'Purpleleaf'.
- *Parentage.*—Mother Plant *Davidia involucrata* (unnamed, unpatented). Father Plant *Davidia involucrata* (unnamed, unpatented).
- *Propagation.*—Grafting.

Plant:
- *Typical size.*—20 meters tall.
- *Observed size.*—1.5 meters tall.
- *Habit.*—Upright, pyramidal.

Branches:
- *Lateral branches.*—8 to 10.
- *Size.*—Diameter: Base 10 to 20 mms; Apex 2–3 mms. Color: Near Grey-Brown Group N199A. Texture: Glabrous. Color of New Shoots: Near Brown Group 200B–C.

Leaf:

*Shape.*—Broadly ovate. Base: Cordate to dentate. Apex: Acuminate.

*Leaf size.*—8 to 14 cms long and 5 to 8 cms wide.

*Arrangement.*—Alternate.

*Margin.*—Entire.

*Texture/substance.*—Glossy and glabrous above and densely tomentose beneath.

*Color.*—Young Foliage Upper side: Near Purple Group 79A–B. Mature Foliage: Upper side: Near 79B with slight coloration of Green Group 136C.

*Venation.*—Pattern: Upper Surface Impressed.

*Petioles.*—Size: 7.5 cms long; 1 to 2 mm wide. Color: Near Brown Group 200B. Texture: Smooth.

*Internodes.*—3 to 8 cms.

*Hardiness.*—USDA Zone 5 (−20° F. to −10° F.).

*Vigor.*—Moderate.

*Pests/diseases.*—None noted.

Inflorescence. None yet observed.

I claim:

1. A new and distinct *Davidia involucrata* plant of the variety substantially as shown and described.

* * * * *